United States Patent [19]
Ohkoshi et al.

[11] Patent Number: 5,679,847
[45] Date of Patent: Oct. 21, 1997

[54] PROCESS FOR PRODUCING TEREPHTHALIC ACID

[75] Inventors: Fumio Ohkoshi; Masato Inary; Fumiya Zaima, all of Kurashiki, Japan

[73] Assignees: Mitsubishi Gas Chemical Company, Inc., Tokyo; Toyo Boseki Kabushiki Kaisha, Osaka; Mizushima Aroma Company, Ltd., Kurashiki, all of Japan

[21] Appl. No.: 642,874

[22] Filed: May 6, 1996

[30] Foreign Application Priority Data

May 30, 1995  [JP]  Japan .................. 7-131303

[51] Int. Cl.⁶ .................................. C07C 51/16
[52] U.S. Cl. .................................. 562/416
[58] Field of Search .................................. 562/416

[56] References Cited

U.S. PATENT DOCUMENTS

| | | |
|---|---|---|
| 4,211,882 | 7/1980 | Komatsu .................. 562/416 |
| 4,214,100 | 7/1980 | Komatsu .................. 562/416 |

FOREIGN PATENT DOCUMENTS 1 508 241   4/1978   United Kingdom .

*Primary Examiner*—Michael L. Shippen
*Attorney, Agent, or Firm*—Frishauf, Holtz, Goodman, Langer & Chick, P.C.

[57] ABSTRACT

There is disclosed a process for producing terephthalic acid which comprises oxidizing in a liquid-phase a starting raw material comprising p-xylene incorporated with 3 to 35% by weight of p-tolualdehyde based on the same at a temperature in the range of 120° to 240° C. by means of a molecular oxygen-containing gas by using a lower aliphatic monocarboxylic acid as a solvent in the presence of a catalyst comprising a manganese compound having 50 to 1000 ppm by weight of manganese atoms, a cobalt compound having 50 to 2000 ppm by weight of cobalt atoms and a bromine compound having 100 to 4000 ppm by weight of bromine atoms, each based on the solvent. By virtue of the above specific constitution, it is made possible to produce high-quality terephthalic acid with a high residual rate of the lower aliphatic monocarboxylic acid as a solvent minimized in its loss, thereby enabling the production of high-quality polyester with high whiteness from the above terephthalic acid and a glycol.

16 Claims, No Drawings

PROCESS FOR PRODUCING TEREPHTHALIC ACID

BACKGROUND OF THE INVENTION

1. Field of the Invention

The present invention relates to a process for producing terephthalic acid by oxidizing the mixture of p-xylene and p-tolualdehyde as the starting raw material by the use of a molecular oxygen-containing gas by using a lower aliphatic monocarboxylic acid as a solvent in the presence of a heavy metal compound and a bromine compound.

2. Description of Related Arts

There is disclosed, in Japanese Patent Publication No. 2666/1959, a process for producing an aromatic carboxylic acid by oxidizing, in a liquid phase, an aromatic compound having at least one aliphatic substituent group by the use of a molecular oxygen-containing gas by using a lower aliphatic monocarboxylic acid as a solvent in the presence of a heavy metal compound containing manganese and a bromine compound to produce the corresponding aromatic carboxylic acid. The process disclosed in the above-mentioned patent publication, which is a process for producing an aromatic carboxylic acid from the corresponding aromatic compound having at least one aliphatic substituent group in a single reaction step by applying the hydrogen withdrawing function of bromine ions to the reaction, has been industrialized as a process for producing terephthalic acid from p-xylene, thus accumulating long years of actual results in plenty of production plants with commercial scale.

On the other hand, as a process for producing an aromatic carboxylic acid by the use of an aromatic compound having at least one aliphatic substituent group other than p-xylene as a starting raw material, consideration is given to a production process using, as a starting raw material, p-tolualdehyde, p-toluic acid or 4-carboxybenzaldehyde (4 CBA) which is an intermediate in the reaction wherein p-xylene is oxidized into terephthalic acid. The above-mentioned p-tolualdehyde is industrially produced by a process in which toluene and carbon monoxide are reacted into p-tolualdehyde in the presence of $HF \cdot BF_3$ as a catalyst (refer to Japanese Patent Publication No. 29760/1964). It is also described in Japanese Patent Publication No. 44653/1982 (GB 1518881) which discloses a process for synthesizing terephthalic acid in a semicontinuous or continuous reaction step by oxidizing p-tolualdehyde in a reaction system comprising itself, a publicly known cobalt compound, manganese compound, bromine compound and lower aliphatic monocarboxylic acid.

Although p-tolualdehyde is an intermediate in the process for synthesizing terephthalic acid by oxidizing p-xylene as a starting raw material, blackened terephthalic acid is produced as the case may be in the semicontinuous or continuous reaction process described in the foregoing Japanese Patent Publication No. 44653/1982. Such a phenomenon has never been observed in the case where terephthalic acid is synthesized by the oxidation of p-xylene.

It is impossible to obtain a polyester which preserves whiteness and transparency and deserves being a commodity by reacting such blackened terephthalic acid as it is with a glycol. In addition, such blackened terephthalic acid cannot be discolored by any of the publicly known methods including washing with acetic acid, crystallization from acetic acid or water, recrystallization from hot water accompanied by hydrogenation as disclosed in Japanese Patent Publication No. 16860/1966, and the like.

It is difficult, therefore, to produce terephthalic acid having a quality comparable to that of the terephthalic acid produced from p-xylene, when any of the conventional methods is employed in semicontinuous or continuous reaction process for producing the same by using p-tolualdehyde instead of p-xylene as a starting raw material.

The primary cause for the blackening is the precipitation of a manganese oxide in terephthalic acid crystal, and accordingly, the extent of the contamination of a manganese oxide in terephthalic acid depends greatly on the concentration of water or manganese in the reactants.

There are proposed, on the basis of the above-mentioned finding and information, processes for producing terephthalic acid having high whiteness by a method in which the water concentration in the reaction mother liquor is suppressed to 10% or less in the case of oxidizing p-tolualdehyde (refer to Japanese Patent Publication No. 44653/1982), a method in which the manganate concentration in the reaction mother liquor is controlled to at most 40 ppm (refer to Japanese Patent Publication No. 5777/1982 (GB 1518901)), and the like methods.

Moreover, there are also proposed, as related patents, a method in which p-tolualdehyde is oxidized in a liquid phase with a molecular oxygen-containing gas by using a lower aliphatic monocarboxylic acid as a solvent in the presence of a catalyst comprising all of (I) a manganese compound, (II) a cobalt compound, (III) a bromine compound and (IV) a metal belonging to lanthanum series (refer to Japanese Patent Publication No. 28900/1981) and a method in which p-tolualdehyde is oxidized in a liquid phase with a molecular oxygen-containing gas by using a lower aliphatic monocarboxylic acid as a solvent in the presence of a catalyst comprising (I) a manganese compound, (II) a cobalt compound, (III) a bromine compound and (IV) at least one compound selected from the group consisting of iron compounds, nickel compounds and chromium compounds (refer to Japanese Patent Publication No. 28899/1981 (GB 1505453)).

Furthermore there is disclosed, in Japanese Patent Publication No. 28897/1981 (GB 1508241), a process for producing terephthalic acid by oxidizing p-tolualdehyde in a liquid phase with a molecular oxygen-containing gas by using a lower aliphatic monocarboxylic acid as a solvent in the presence of a heavy metal salt including a manganese salt and a bromine compound as the catalysts which process comprises adding, to the p-tolualdehyde as a starting raw material, an alkylbenzene (mainly p-xylene) in an amount satisfying the relational expression $$M \leq -0.15A^2 + 15A + 40 \quad 0 < A \leq 50$$

where M is the concentration of atomic manganese in ppm by weight in the reaction mother liquor and A is the amount of the alkylbenzene (mainly p-xylene) in % by weight to be added to the p-tolualdehyde.

Such being the case, the troubles in the aspect of reaction conditions have already been overcome in the process for producing terephthalic acid by oxidizing p-tolualdehyde as the starting raw material with a molecular oxygen-containing gas by using a lower aliphatic monocarboxylic acid as a solvent in the presence of a heavy metal compound and a bromine compound. There has already been established, in the practical production procedure, a technical follow-up such as a measure for the necessity of interrupting the contact of oxygen with p-tolualdehyde as the starting raw material until it is introduced into an oxidization reactor (refer to Japanese Patent Publication No. 16133/1981), thereby enabling the process for producing terephthalic acid from p-tolualdehyde as the starting raw material to be put into practice in an industrial production scale.

The process for producing terephthalic acid from p-tolualdehyde as the starting raw material, when compared with the prevailing process for producing the same from p-xylene as the starting raw material, is enhanced in its economical effect in that terephthalic acid can be produced without passing through the complicated step and procedure of separating p-xylene from mixed xylene, and also is considered to be advantageous in that the oxygen demand in the course of oxidation step can be economized, since p-tolualdehyde is an intermediate in the conversion of p-xylene to terephthalic acid.

In the process for producing terephthalic acid by the use of a lower aliphatic monocarboxylic acid as a solvent, part of the solvent is oxidized in the course of liquid-phase oxidation, and therefore, it is required to minimize the solvent loss due to oxidation. Moreover in recent years, terephthalic acid with higher quality has been required, whereby a suitable measure is urged in the production process of terephthalic acid using p-xylene or p-tolualdehyde as the starting raw material.

In view of the foregoing, it is an object of the present invention to provide a process for producing terephthalic acid using a lower aliphatic monocarboxylic acid as a solvent which process is characterized in that the solvent loss is minimized and the quality of the objective terephthalic acid is further enhanced.

SUMMARY OF THE INVENTION

As a result of intensive research and investigation made by the present inventors on the process for producing terephthalic acid involved with the above-mentioned problem to be solved, it has been found that the objective terephthalic acid is improved in quality in addition to decrease in the oxidation loss of a lower aliphatic monocarboxylic acid to be used as the solvent by mixing a specific amount of p-tolualdehyde with p-xylene as a starting raw material to carry out the liquid-phase oxidation reaction. The present invention has been accomplished on the basis of the above-mentioned finding.

Specifically, the present invention is concerned with a process for producing terephthalic acid which comprises oxidizing in a liquid-phase a starting raw material comprising p-xylene incorporated with 3 to 35% by weight of p-tolualdehyde based on the same at a temperature in the range of 120° to 240° C. by means of a molecular oxygen-containing gas by using a lower aliphatic monocarboxylic acid as a solvent in the presence of a catalyst comprising a manganese compound having 50 to 1000 ppm by weight of manganese atoms, a cobalt compound having 50 to 2000 ppm by weight of cobalt atoms and a bromine compound having 100 to 4000 ppm by weight of bromine atoms, each based on said solvent.

DESCRIPTION OF PREFERRED EMBODIMENT

There are used, compounds of manganese, cobalt and bromine, respectively as a catalyst in the present invention. Any of inorganic acid salts and organic acid salts are usable as the metallic salt of manganese or cobalt, and is preferably used in the form of a compound soluble in a reaction solvent. It is preferable that the amount of a manganate be at least 50 ppm by weight expressed in terms of manganese atoms based on the solvent in order to attain a sufficient catalyst effect, but a manganate content exceeding 1000 ppm by weight expressed in terms of manganese atoms based on the solvent unfavorably causes a fear of forming blackened terephthalic acid. The amount of a cobalt salt to be used is preferably in the range of 50 to 2000 ppm by weight expressed in terms of cobalt atoms based on the solvent. As usable bromine compounds, mention is made of inorganic salts of bromine with ammonium, sodium, potassium or the like and hydrogen bromide, and besides organic bromine compounds such as tetrabromoethane and tetrabromo-p-xylene. The amount of a bromine compound to be used is preferably in the range of 100 to 4,000 ppm by weight expressed in terms of bromine atoms based on the solvent.

Examples of lower aliphatic monocarboxylic acids usable as a solvent include acetic acid, propionic acid and butyric acid, among which acetic acid is particularly favorable. A sufficient amount of the solvent to be used is at least double by weight of the starting raw material.

The reaction temperature in liquid-phase oxidation is in the range of 120° to 240° C. In order that the reaction may be carried out in a liquid phase, the reaction system usually needs to be pressurized so as to maintain the starting raw material as well as the solvent in a liquid phase. Hence a reaction pressure in the range of 1 to 50 atm is usually used.

There is used, as an oxidizing agent, molecular oxygen or a molecular oxygen-containing gas, and the use of air is economically advantageous.

The liquid-phase oxidation reaction according to the present invention is semicontinuously or continuously put into practice, and the reaction conditions such as the feed rates of the starting raw material and air and retention time of the reaction liquid in a reaction vessel in the case of continuous process fall within the range almost the same as that of the publicly known technique.

In order to attain the object of the present invention, that is, to decrease the oxidation loss of the solvent and to improve the quality of the objective terephthalic acid, the proportion of p-tolualdehyde to be mixed with p-xylene is 3 to 35%, preferably 10 to 25% by weight based on p-xylene as the starting raw material. As will be shown in the under-mentioned working examples and comparative examples, the mixing ratio of p-tolualdehyde in the above-mentioned range not only minimizes the oxidation loss of the solvent, but also improves the quality of the resultant terephthalic acid.

There is favorably usable in the process according to the present invention, p-tolualdehyde which is synthesized from toluene and carbon monoxide according to Gattermann-Koch reaction in the presence of HF.BF3 catalyst, but there is essentially no restriction at all to the process for producing p-tolualdehyde. Since the p-tolualdehyde which is produced in the presence of $HF.BF_3$ catalyst contains about 5% of o-tolualdehyde because of the reactional characteristics, the mixture of isomers is distilled or crystallized to separate o-isomer from p-tolualdehyde, which is usually used as the starting raw material. Alternatively, the p-tolualdehyde containing o-isomer may be used as it is as the starting raw material depending on the situation.

The resultant terephthalic acid is usually subjected to a hydrogenating purifying treatment to make it into highly pure terephthalic acid, most of which is made into a polyester for commercial use through polycondensation step. The terephthalic acid produced through the process according to the present invention is characterized in that a polyester made therefrom is excellent in whiteness.

As can be seen from the under-mentioned working examples and comparative examples, when p-tolualdehyde is mixed with p-xylene as the starting raw material, $OD_{340}$ value of highly pure terephthalic acid obtained by purification does not vary in particular as compared with p-xylene alone, but a polyester formed by polycondensation between the highly pure terephthalic acid and ethylene glycol is improved in whiteness.

$OD_{340}$, which stands for the absorbance (optical density) at 340 nm wavelength of an alkali solution of terephthalic acid, is widely used in the stage of terephthalic acid as a simple-convenient index for the presumption of the whiteness of a polymer to be produced therefrom. It cannot be said, however, that there always exists an obvious relationship between $OD_{340}$ and the whiteness of the polymer. The survey of numerous investigation results accumulated so far on $OD_{340}$ and polymer whiteness has revealed that the polymer whiteness can be presumed from $OD_{340}$ in a specific production plant and within a generally specified range of operational conditions.

Judging comprehensively from the aforesaid finding and information, it is understood that the mixing of p-tolualdehyde in p-xylene clearly causes qualitatively different reaction, but details of the reaction mechanism still remain unknown.

In the following, the present invention will be described in more detail with reference to comparative examples and working examples, which however, shall not be construed to limit the present invention thereto.

p-Tolualdehyde which was used in the following working examples and comparative examples had been synthesized from toluene and carbon monoxide in the presence of $HF.BF_3$ catalyst according to Gattermann-Koch reaction, followed by removal of o-tolualdehyde by means of distillation. The storage and use of the p-tolualdehyde and the mixture of the same and p-xylene were carried out by sealing with gaseous nitrogen to prevent them from coming into contact with air.

It is necessary in the comparison between working examples and comparative examples to set the degree of progress of the oxidation reaction to approximately the same level. Accordingly, 4 CBA concentration of 820 ppm in terephthalic acid which had been obtained from p-xylene alone as the starting raw material in Comparative Example 1 was taken as the standard for the degree of progress of the oxidation reaction, and the reaction temperature was regulated so as to attain the concentration of 4 CBA almost the same as that of the standard (820 ppm, approx.) in each of the working examples and comparative examples.

In the following working examples and comparative examples, the residual amount of acetic acid in the filtrate (oxidation mother liquor) was determined by gas chromatography, and divided by the charged amount thereof to represent the residual rate of acetic acid in percentage.

$OD_{340}$ was found by dissolving 3.2 g of highly pure terephthalic acid in 40 milliliter (mL) of 2N aqueous solution of potassium hydroxide and measuring the absorbance of the solution at 340 nm by the use of water as the control in a cell with 50 mm length.

Co-b value which stands for the yellowness of the polymer was found by measuring the color tone of the polymer in the form of chip by the use of an automatic color computer (produced by Tokyo Denshoku Co., Ltd. under the trade name "TC-1500").

The quality of terephthalic acid was evaluated as follows.

A 2 liter (L) stainless steel-made pressure resistant vessel equipped with a stirrer, a heater, a gas introducing port and a catalyst cage of magnetic type which can be raised and lowered from outside was charged with 300 g of terephthalic acid obtained by the oxidation reaction and 900 g of pure water. The catalyst cage was packed with palladium/carbon catalyst in an amount of 16 g on wet basis which had been continuously used for about one year in a commercial scale hydrofining apparatus, and thereafter the catalyst was washed with dilute aqueous ammonia to remove contaminants and then thoroughly washed with water.

Subsequently, hydrogen gas was introduced into the vessel through a gas introducing pipe to sufficiently replace the atmosphere in the vessel with hydrogen by purging several times and fill in the vessel with hydrogen to a pressure of 10 $kg/cm^2G$, while the catalyst cage was suspended at the top of the vessel. Temperature raising in the vessel was started under stirring and, after confirming the temperature stabilized at 282° C., the catalyst cage was lowered so as to settle in the liquid. After the elapse of 20 minutes, the catalyst cage was raised and then the temperature was lowered to room temperature, approximately to form a cooled slurry, which was filtered with a glass filter to form cake. After washing the resultant cake with pure water at about 90° C., the cake was dried at 110° C. to afford highly pure terephthalic acid, and a measurement was made of $OD_{340}$ value thereof.

A stainless steel-made autoclave equipped with a stirrer, a still and a pressure regulator was charged with 100 g of highly pure terephthalic acid and 82 g of ethylene glycol, and further with 0.05 g of antimony trioxide and 0.2 g of triethylamine. Subsequently, esterification reaction was carried out at a pressure raised to 2.5 $kg/cm^2G$ with nitrogen and at a temperature raised to 230° C. under stirring. The reaction was continued for 2 hours, while water formed by reaction was consecutively removed, and subsequently the temperature in the reaction system was raised to 275° C. for one hour, while the pressure in the system was gradually reduced to 0.1 mmHg. Under the reaction conditions as mentioned above, polycondensation reaction was carried out for 2 hours, while the ethylene glycol formed by the reaction was consecutively removed. The polymer thus formed was taken out and placed into water to form strand, which was cut with a cutter into pieces in the form of chip. Thus, a measurement was made of Co-b value showing the yellowness of the polymer.

EXAMPLE 1

To a 2 L titanium-made pressure resistant reactor equipped with a reflux condenser, a stirrer, a heater, a raw material feed port and a gas introducing port were fed in advance, a catalyst comprising 3.16 g of cobalt acetate tetrahydrate, 0.636 g of manganese acetate tetrahydrate and 1.296 g of hydrobromic acid and 840 g of acetic acid, corresponding to 890 ppm cobalt, 170 ppm manganese and 1200 ppm bromine, respectively expressed in term of atom.

The reactor charged with the catalyst and acetic acid was pressurized with nitrogen at 20 $kg/cm^2G$, and was heated to raise the temperature up to 200° C. with the heater. Then p-xylene containing p-tolualdehyde in a proportion of 20% by weight was continuously fed in the reactor at a constant feed rate for one hour making a total amount of 320 g to proceed with the reaction under the reaction conditions of 200° C. temperature and 20 $kg/cm^2G$ pressure, while air was continuously blown into the reactor. After the stoppage of the starting raw material feeding, air was blown thereinto for 5 minutes and thereafter, the reactor was cooled to discharge the content in the reactor.

As the breakdown of the total amount of the starting raw material fed in the reactor for one hour, p-tolualdehyde and p-xylene were fed in amounts of 64 g (0.532 mol) and 256 g (2.411 mol), respectively, making a total of 320 g.

The resultant slurry was cooled to room temperature, filtered with a glass filter to recover the cake, which was washed with acetic acid and water and thereafter dried at 110° C. to obtain 472.8 g (2.846 mol) of terephthalic acid.

The objective terephthalic acid was obtained at 96.7% by mol yield based on the starting raw material used with residual rate of acetic acid of 93.6% and 4 CBA concentration of 780 ppm in the objective terephthalic acid.

In addition, highly pure terephthalic acid obtained by purifying the above-produced terephthalic acid had an $OD_{340}$ value of 0.098 and a polyester produced therefrom had a Co-b value of 0.81.

EXAMPLE 2

The procedure in Example 1 was repeated except that the content of p-tolualdehyde in the starting raw material was set to 10% by weight instead of 20% by weight.

The objective terephthalic acid was obtained at 97.3% by mol yield based on the starting raw material used with residual rate of acetic acid of 91.8% and 4 CBA concentration of 840 ppm in the objective terephthalic acid. Highly pure terephthalic acid obtained by purifying the above-produced terephthalic acid had an $OD_{340}$ value of 0.103 and a polyester produced therefrom had a Co-b value of 0.83.

EXAMPLE 3

The procedure in Example 1 was repeated except that the content of p-tolualdehyde in the starting raw material was set to 5% by weight instead of 20% by weight and that the reaction temperature was set to 205° C. instead of 200° C.

The objective terephthalic acid was obtained at 96.6% by mol yield based on the starting raw material used with residual rate of acetic acid of 90.5% in the objective terephthalic acid. Highly pure terephthalic acid obtained by purifying the above-produced terephthalic acid had an $OD_{340}$ value of 0.096 and a polyester produced therefrom had a Co-b value of 0.91.

Comparative Example 1

The procedure in Example 1 was repeated except that p-tolualdehyde was not incorporated in the starting raw material and that the reaction temperature was set to 205° C. instead of 200° C.

The objective terephthalic acid was obtained at 96.1% by mol yield based on the starting raw material used with residual rate of acetic acid of 87.3% and 4 CBA concentration of 820 ppm in the objective terephthalic acid. Highly pure terephthalic acid obtained by purifying the above-produced terephthalic acid had an $OD_{340}$ value of 0.097 and a polyester produced therefrom had a Co-b value of 1.08.

Comparative Example 2

The procedure in Example 1 was repeated except that the content of p-tolualdehyde in the starting raw material was set to 40% by weight instead of 20% by weight and that the reaction temperature was set to 195° C. instead of 200° C.

The objective terephthalic acid was obtained at 97.6% by mol yield based on the starting raw material used with residual rate of acetic acid of 88.8% and 4 CBA concentration of 790 ppm in the objective terephthalic acid. Highly pure terephthalic acid obtained by purifying the above-produced terephthalic acid had an $OD_{340}$ value of 0.100 and a polyester produced therefrom had a Co-b value of 0.80.

Comparative Example 3

The procedure in Example 1 was repeated except that the content of p-tolualdehyde in the starting raw material was set to 60% by weight instead of 20% by weight and that the reaction temperature was set to 190° C. instead of 200° C.

The objective terephthalic acid was obtained at 96.5% by mol yield based on the starting raw material used with residual rate of acetic acid of 88.1% and 4 CBA concentration of 770 ppm in the objective terephthalic acid. Highly pure terephthalic acid obtained by purifying the above-produced terephthalic acid had an $OD_{340}$ value of 0.096 and a polyester produced therefrom had a Co-b value of 0.82.

The results of each of the above-mentioned examples and comparative examples are collectively given in Table 1, wherein p-tolualdehyde is abbreviated to pTAL; terephthalic acid to TA; 4-carboxybenzaldehyde to 4 CBA; highly pure terephthalic acid to PTA; and polyester to PE.

TABLE 1

| | Mixing ratio of pTAL | Reaction temperature | Yield of TA | 4 CBA in TA | Residual rate of acetic acid | $OD_{340}$ value of PTA | Co-b value in PE |
|---|---|---|---|---|---|---|---|
| Example 1 | 20% | 200° C. | 96.7% | 780 ppm | 93.6% | 0.098 | 0.81 |
| Example 2 | 10% | 200° C. | 97.3% | 840 ppm | 91.8% | 0.103 | 0.83 |
| Example 3 | 5% | 205° C. | 96.6% | 720 ppm | 90.5% | 0.096 | 0.91 |
| Comparative Example 1 | 0% | 205° C. | 96.1% | 820 ppm | 87.3% | 0.097 | 1.08 |
| Comparative Example 2 | 40% | 195° C. | 97.6% | 790 ppm | 88.8% | 0.100 | 0.80 |
| Comparative Example 3 | 60% | 195° C. | 96.5% | 770 ppm | 88.1% | 0.096 | 0.82 |

As is clearly understood from the results given in Table 1, in the case of using p-xylene mixed with p-tolualdehyde as the starting raw material, a trend towards lowering of the oxidation reaction temperature is observed and the residual rate of acetic acid is improved, while the yield of terephthalic acid and 4 CBA concentration in the objective terephthalic acid keep approximately the same level, respectively. However, a mixing rate or content of p-tolualdehyde of 40% by weight lessens the predominancy of the residual rate of acetic acid (refer to Comparative Example 2). That is to say, it can be seen that the residual rate of acetic acid as the function of the mixing rate of p-tolualdehyde takes a maximum value. There is only a small difference in the residual rate of acetic acid between a mixing rate of p-tolualdehyde of 60% by weight (experimental result in Comparative Example 3) and that of zero %, that is, p-xylene alone (Comparative Example 1) (88.1% vs. 87.3%). On the other hand, highly pure terephthalic acid which is obtained by hydrofining raw terephthalic acid does not show an appreciable difference in $OD_{340}$ value whether or not p-xylene as the starting raw material is mixed with p-tolualdehyde. Nevertheless, there is clearly observed a tendency towards decrease in Co-b value of the polyester which is obtained by the polycondensation of the highly pure terephthalic acid and ethylene glycol in the case where p-xylene as the starting raw material is mixed with p-tolualdehyde.

What is claimed is:

1. A process for producing terephthalic acid which comprises oxidizing in a liquid-phase a starting raw material comprising p-xylene and 3 to 35% by weight of p-tolualdehyde at a temperature of 120° to 240° C. in the presence of (a) a molecular oxygen-containing gas, (b) a solvent, said solvent being a lower aliphatic monocarboxylic acid and (c) a catalyst comprising (i) a manganese compound having 50 to 1000 ppm by weight of manganese atoms based on the amount of said solvent, (ii) a cobalt compound having 50 to 2000 ppm by weight of cobalt atoms based on the amount of said solvent and (iii) a bromine compound having 100 to 4000 ppm by weight of bromine atoms, based on the weight of said solvent.

2. The process for producing terephthalic acid according to claim 1 wherein the p-tolualdehyde is in an amount of 10 to 25% by weight.

3. The process for producing terephthalic acid according to claim 1 wherein the lower aliphatic monocarboxylic acid is selected from the group consisting of acetic acid, propionic acid and butyric acid.

4. The process for producing terephthalic acid according to claim 3 wherein the lower aliphatic monocarboxylic acid is acetic acid.

5. The process for producing terephthalic acid according to claim 1 wherein the lower aliphatic monocarboxylic acid is used in an amount of at least double by weight of the starting raw material.

6. The process for producing terephthalic acid according to claim 1 wherein the process is carried out at a pressure of 1 to 50 atm.

7. The process for producing terephthalic acid according to claim 1 wherein the molecular oxygen-containing gas is selected from the group consisting of molecular oxygen and air.

8. The process for producing terephthalic acid according to claim 1 wherein the bromine compound is selected from the group consisting of hydrogen bromide, tetrabromoethane, tetrabromo-p-xylene and an inorganic salt of bromine with ammonium, sodium or potassium.

9. The process for producing terephthalic acid according to claim 2 wherein the lower aliphatic monocarboxylic acid is acetic acid.

10. The process for producing terephthalic acid according to claim 9 wherein the acetic acid is in an amount of at least double by weight of the starting raw material.

11. The process for producing terephthalic acid according to claim 10 wherein the process is carried out at a pressure of 1 to 50 atm and the molecular oxygen containing gas is selected from the group consisting of molecular oxygen and air.

12. The process for producing terephthalic acid according to claim 6 wherein the cobalt compound is cobalt acetate tetrahydrate, the manganese compound is manganese acetate tetrahydrate, the bromine compound is hydrobromic acid, the lower aliphatic monocarboxylic acid is acetic acid and the molecular oxygen-containing gas is air.

13. The process for producing terephthalic acid according to claim 12 wherein the p-tolualdehyde is in an amount of 20% by weight.

14. The process for producing terephthalic acid according to claim 12 wherein the p-tolualdehyde is in an amount of 10% by weight.

15. The process for producing terephthalic acid according to claim 12 wherein the p-tolualdehyde is in an amount of 5% by weight.

16. The process for producing terephthalic acid according to claim 12 wherein the temperature is 200° C. and the pressure is 20 kg/cm$^2$G.

* * * * *